(12) United States Patent
Chen et al.

(10) Patent No.: US 8,236,967 B2
(45) Date of Patent: Aug. 7, 2012

(54) DIINDENOTHIOPHENE DERIVATIVES AND USE THEREOF

(75) Inventors: Shinn-Horng Chen, Kaohsiung (TW);
Ken-Tsung Wong, Kaohsiung (TW);
Ya-Yan Lin, Kaohsiung (TW);
Shih-Feng Chiu, Kaohsiung (TW);
Jia-Hong Chen, Kaohsiung (TW)

(73) Assignee: Eternal Chemical Co., Ltd., Kaohsiung (TW)

( * ) Notice: Subject to any disclaimer, the term of this patent is extended or adjusted under 35 U.S.C. 154(b) by 368 days.

(21) Appl. No.: 12/648,152

(22) Filed: Dec. 28, 2009

(65) Prior Publication Data

US 2010/0168444 A1    Jul. 1, 2010

(30) Foreign Application Priority Data

Dec. 29, 2008 (TW) .............................. 97151251 A

(51) Int. Cl.
*C07D 333/50* (2006.01)

(52) U.S. Cl. ........................................................ 549/41

(58) Field of Classification Search ..................... 549/41
See application file for complete search history.

(56) References Cited

FOREIGN PATENT DOCUMENTS

CN          101475568 A    *   7/2009

* cited by examiner

*Primary Examiner* — Janet Andres
*Assistant Examiner* — John Mabry
(74) *Attorney, Agent, or Firm* — Shimokaji & Associates, P.C.

(57) ABSTRACT

A diindenothiophene derivative of the following formula (1) is disclosed:

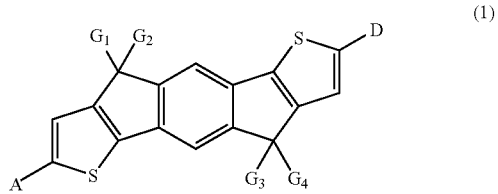

(1)

wherein each of $G_1$, $G_2$, $G_3$ and $G_4$ is independently an unsubstituted or substituted $C_6$-$C_{40}$-aromatic group or a $C_1$-$C_{40}$-aliphatic group; A is an electron-withdrawing group; and D is an electron-donating group. The inventive diindenothiophene derivatives can be used in a dye-sensitized solar cell.

12 Claims, 1 Drawing Sheet

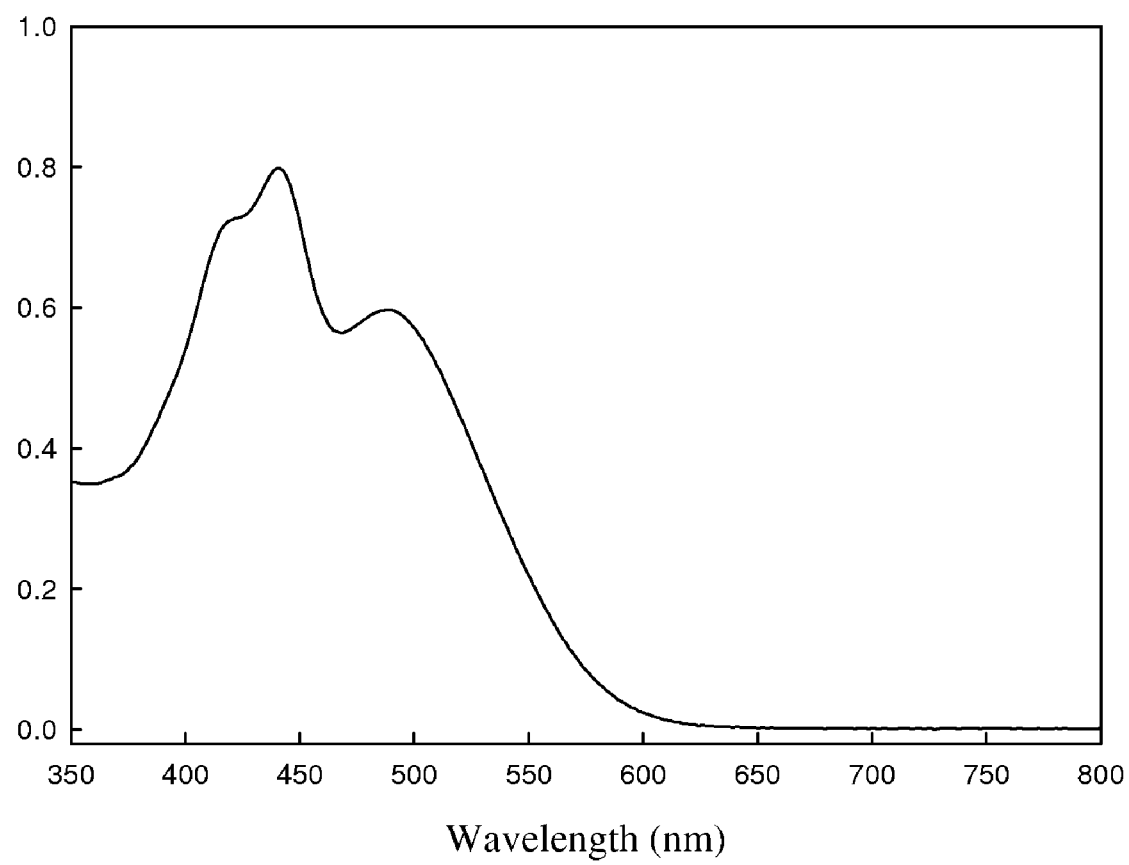

DIINDENOTHIOPHENE DERIVATIVES AND USE THEREOF

BACKGROUND OF THE INVENTION

1. Field of the Invention

The invention pertains to diindenothiophene derivatives that can be used as dyes for dye-sensitized solar cells.

2. Description of the Prior Art

Rapid technological and economic advancements have fostered ever-increasing demand for energy, resulting in declining reserves of petroleum, natural gas, coal, and the like. Meeting this energy demand requires development of new resources. Solar energy is one of the most attractive and important resources for such further development as it generates little or no pollution. Of the many types of solar cells that have been developed to meet this need, dye-sensitized solar cell (DSSC) has the advantages of low manufacturing cost and potential for development.

DSSC was first developed in 1976 by Hiroshi Tsubomura et al. using porous ZnO as an electrode, and achieved a power conversion efficiency of 2.5%. The photoelectric conversion efficiency of DSSC was not substantially increased until 1991, when a Swiss team led by M. Grätzel achieved an efficiency of 7.1~7.9%, opening the door for future commercialization. The DSSC developed by M. Grätzel's team in Switzerland utilized an anode produced by coating $TiO_2$ nano-crystals onto indium-tin-oxide (ITO) glass and had Ru-complex dyes (typically, N3 and N719) absorbed by the porous structure of the porous film formed from the $TiO_2$ nano-crystals to absorb visible light as well as a cathode of a conductive glass plated with platinum, and utilized $I^-/I_3^-$ solution as an electrolyte for providing the oxidation-reduction reaction necessary for the cell. N3 and N719 have the following structures:

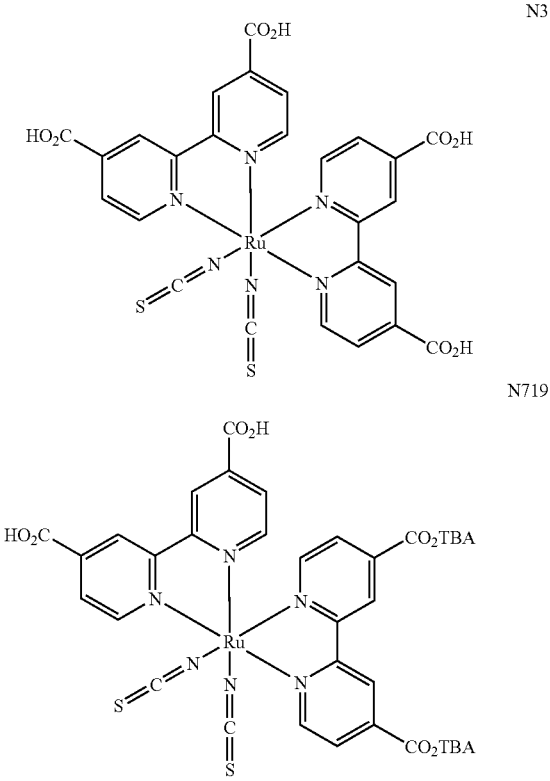

As mentioned above, a dye-sensitized solar cell mainly consists of five parts: a cathode and anode for providing current paths, a $TiO_2$ semiconductor layer for use as an electron transport layer, a dye layer, and an electrolyte for transporting holes. All the materials and the interfacial structures of these parts will play a role in the performance of solar cells. In particular, the dye used in the dye layer is crucial to solar cell efficiency. Therefore, the search for suitable dyes to enhance solar cell efficiency has become an important objective of solar cell development.

Dyes for dye-sensitized solar cells are normally classified into two types: those containing the above-mentioned Ru-complexes, and those comprised of organic molecules. Compared to metal complexes, organic molecules have the following advantages: (1) higher molar absorption coefficient; (2) greater flexibility in structural design and possible range of light absorption; and (3) absence of noble metals, thus eliminating dependence on limited and environmentally hazardous material sources while also reducing production costs.

In 1996, Michael Grätzel employed the natural substance coumarin as a main dye ingredient in a DSSC. However, only 0.9% photoelectric conversion efficiency was achieved, probably due to the relatively narrow absorption band of coumarin preventing efficient utilization of sunlight.

Given the above, there is ongoing demand for organic molecular materials for dyes achieving greater efficiency of sunlight absorption in dye-sensitized solar cells.

SUMMARY OF THE INVENTION

The present invention aims at providing an organic diindenothiophene derivative having a diindenothiophene structure. The diindenothiophene derivatives of the present invention have a high light absorption coefficient and can be used in solar cells as dyes. Moreover, the diindenothiophene derivatives have an absorption spectrum highly overlapping the sunlight spectrum and can obtain a high power conversion efficiency when they are utilized in dye-sensitized solar cells.

Therefore, the present invention also provides a solar cell comprising the above-mentioned diindenothiophene derivative.

BRIEF DESCRIPTION OF THE DRAWING

FIG. 1 is the absorption spectrum of the organic dye compound of formula (2) dissolved in THF according to the present invention.

DETAILED DESCRIPTION OF THE INVENTION

The diindenothiophene derivatives according to the present invention have a structure of the following formula (1):

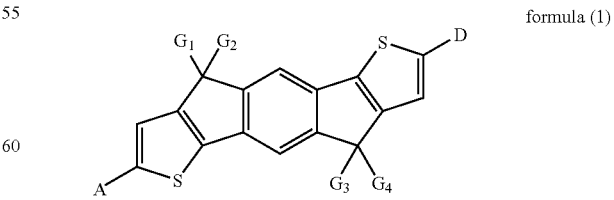

formula (1)

wherein, $G_1$, $G_2$, $G_3$ and $G_4$ are each independently an unsubstituted or substituted $C_6$-$C_{40}$-aromatic group or $C_1$-$C_{40}$-aliphatic group; A is an electron-withdrawing group; and D is an electron-donating group.

According to the present invention, the preferred $G_1$, $G_2$, $G_3$ and $G_4$ are each independently an unsubstituted or substituted $C_6$-$C_{20}$-aromatic group. More preferably, $G_1$, $G_2$, $G_3$ and $G_4$ are each independently a radical selected from the group consisting of the following formula (3), formula (4), formula (5) and formula (6).

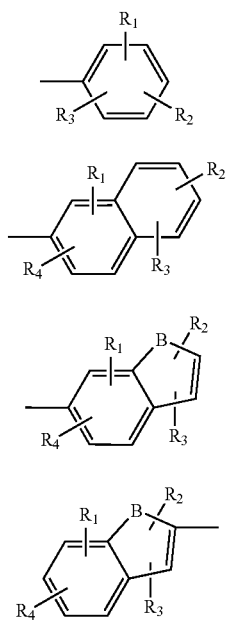

formula (3)

formula (4)

formula (5)

formula (6)

wherein, $R_1$, $R_2$, $R_3$ and $R_4$ are each independently a hydrogen atom, a $C_1$-$C_8$-alkyl, or a $C_1$-$C_8$-alkoxy; and B is $CH_2$, NH, S, Si or O.

According to the present invention, the electron-withdrawing group A is selected from the group consisting of

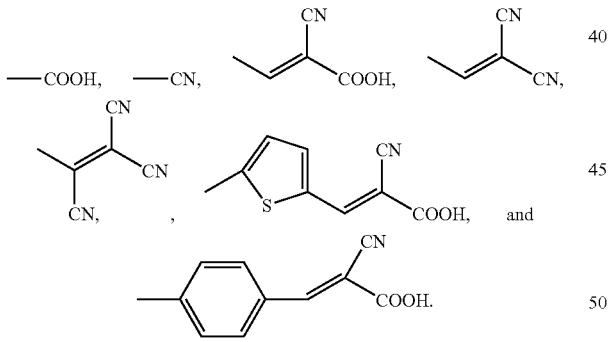

and

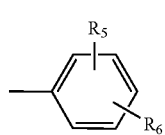

According to the present invention, the electron-donating group D is selected from —N(S¹)(S²) or —C₆H₄—N(S¹)(S²), where S¹ and S² are each independently an unsubstituted or substituted $C_6$-$C_{20}$-aromatic group. According to an embodiment of the present invention, S¹ and S² are each independently selected from the group consisting of the following formula (7), formula (8), formula (9), formula (10), and formula (11):

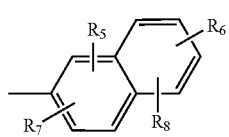

formula (7)

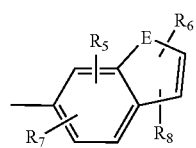

formula (8)

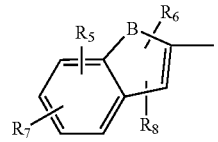

formula (9)

formula (10)

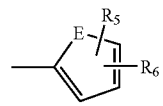

formula (11)

wherein $R_5$, $R_6$, $R_7$ and $R_8$ are each independently a hydrogen atom, a $C_1$-$C_5$-alkyl or a $C_1$-$C_5$-alkoxy; and E is $CH_2$, NH, S, Si or O.

According to a preferred embodiment of the present invention, D is selected from the group consisting of the following:

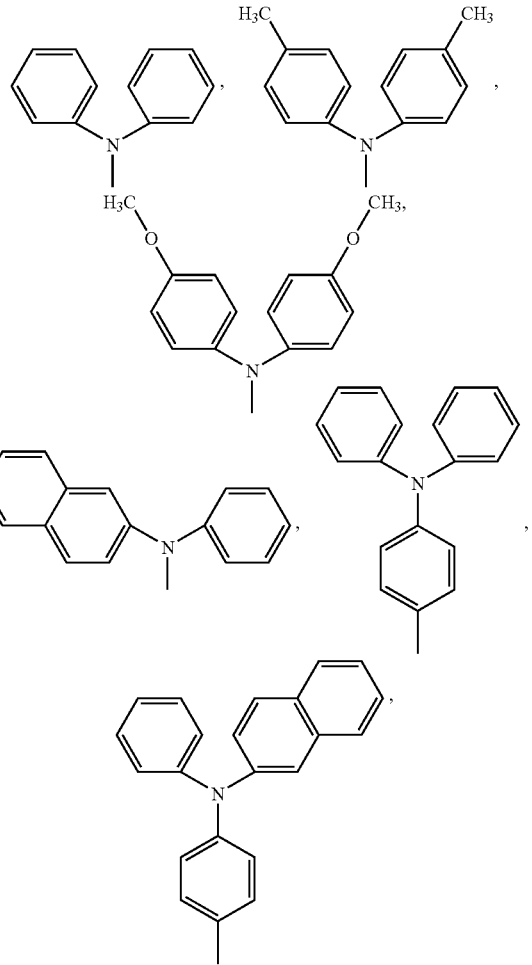

-continued

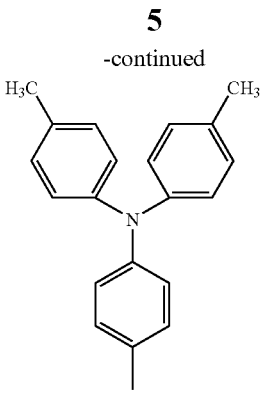

and

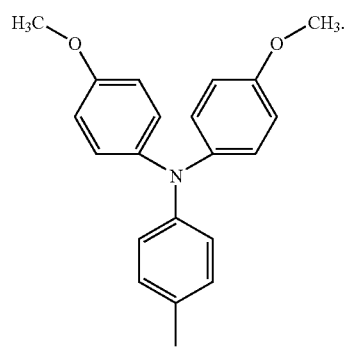

According to another preferred embodiment of the present invention, the $G_1$, $G_2$, $G_3$ and $G_4$ in formula (1) are each independently

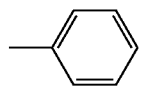 or 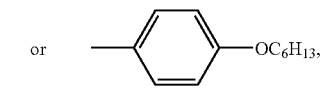, more preferably

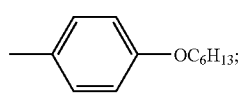;

A is

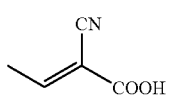 or 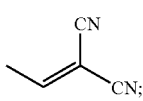;

and D is

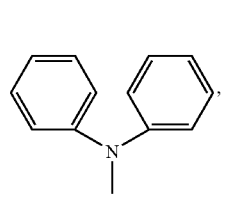, 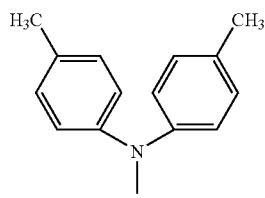 or

-continued

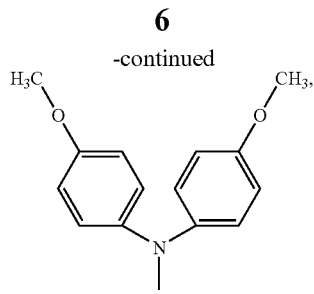

more preferably

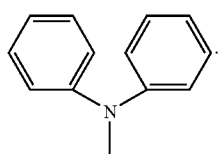

According to a preferred embodiment of the present invention, the diindenothiophene derivatives are of the following formula (2) and formula (3):

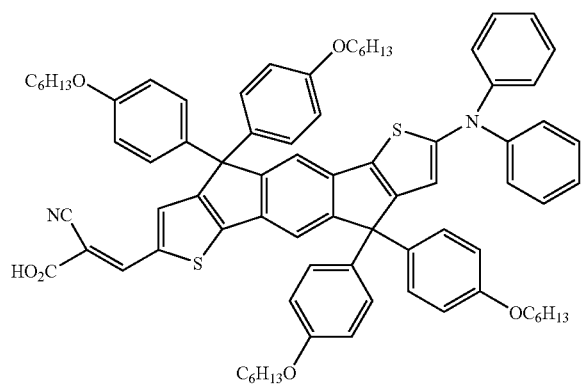

The diindenothiophene derivatives of the present invention can be used in dye-sensitized solar cells as organic dyes. The diindenothiophene derivatives will be fastened on the surface of an oxide semiconductor, such as $TiO_2$, by adsorption. Without being limited by certain theories, it is believed that such organic dye molecules utilize the diindenothiophene group as the molecular center to become ladder-type molecules; utilize the excellent charge carrier mobilities of the thiophene ring and fix many conjugated aromatic rings so as to improve conjugation properties and charge carrier mobilities; and directly inject charges to the conduction bands of the semiconductor with the aid of the electron-donating group, electron-withdrawing group and charge transfer. Moreover, since the diindenothiophene derivatives have a broader absorption band and therefore a high absorption coefficient, they can provide an enhanced light absorption ability. In addition, since a long carbon chain, such as hexyloxyphenyl, is introduced into the molecules, the molecular stability of the molecules can be improved and the molecules will hinder electrolytes from contacting the oxide semiconductor, thereby avoiding the occurrence of dark current and therefore enhancing the efficiency of the solar cells.

The inventive diindenothiophene derivatives can be produced by any of the methods that are conventionally known to persons having ordinary skill in the art. For instance, the above-mentioned compound of formula (2) can be prepared by a method comprising the following steps:

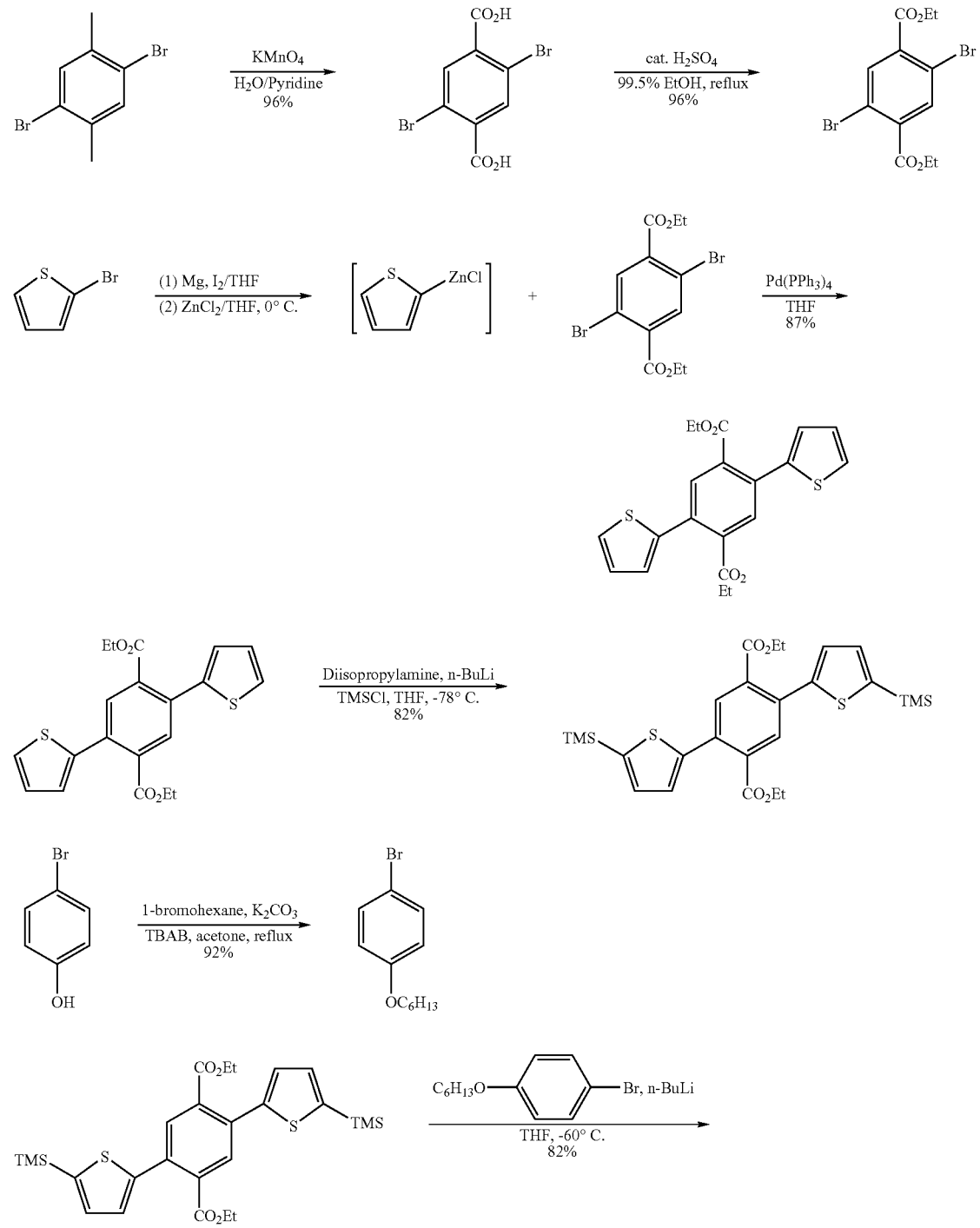

-continued
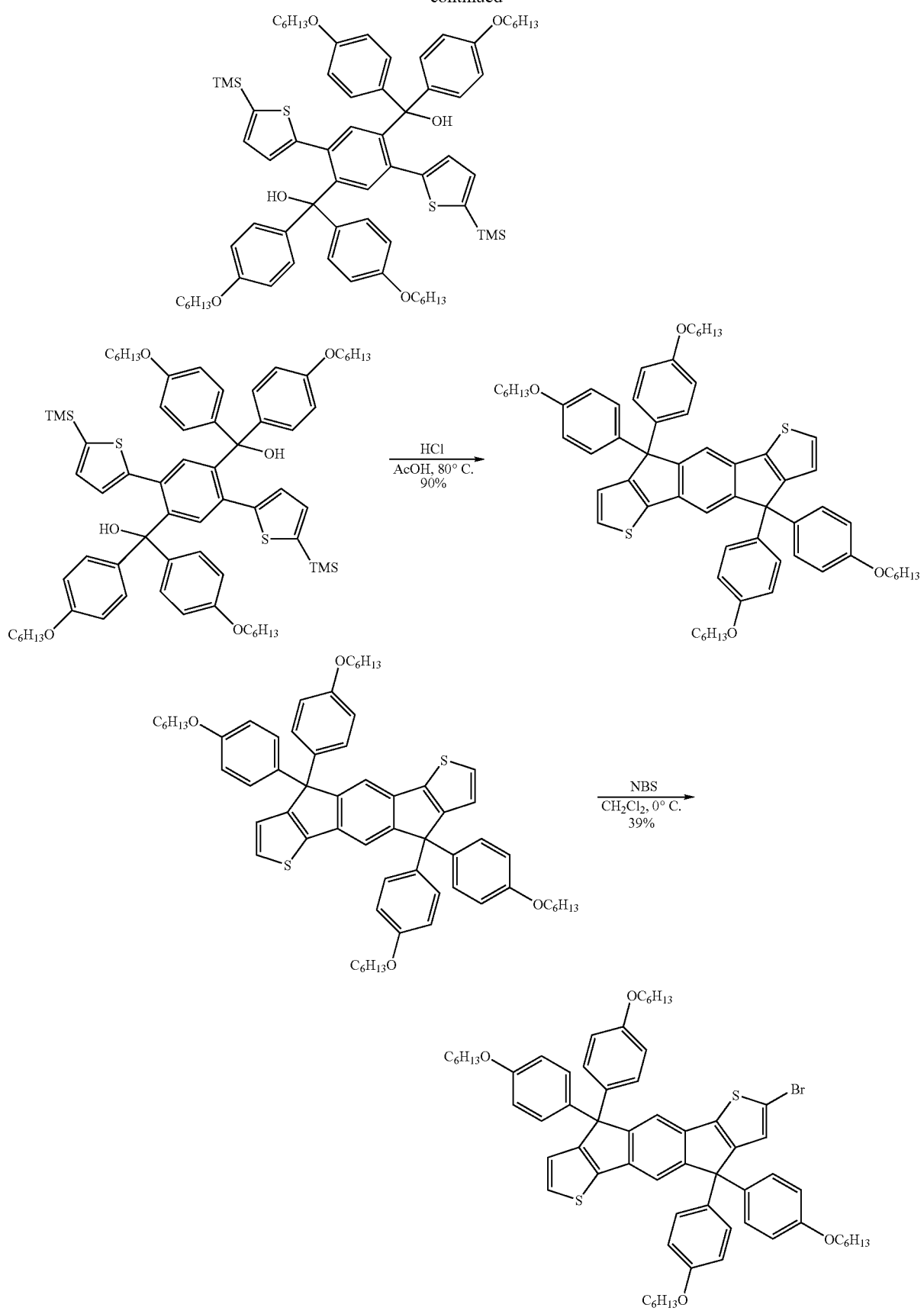

-continued
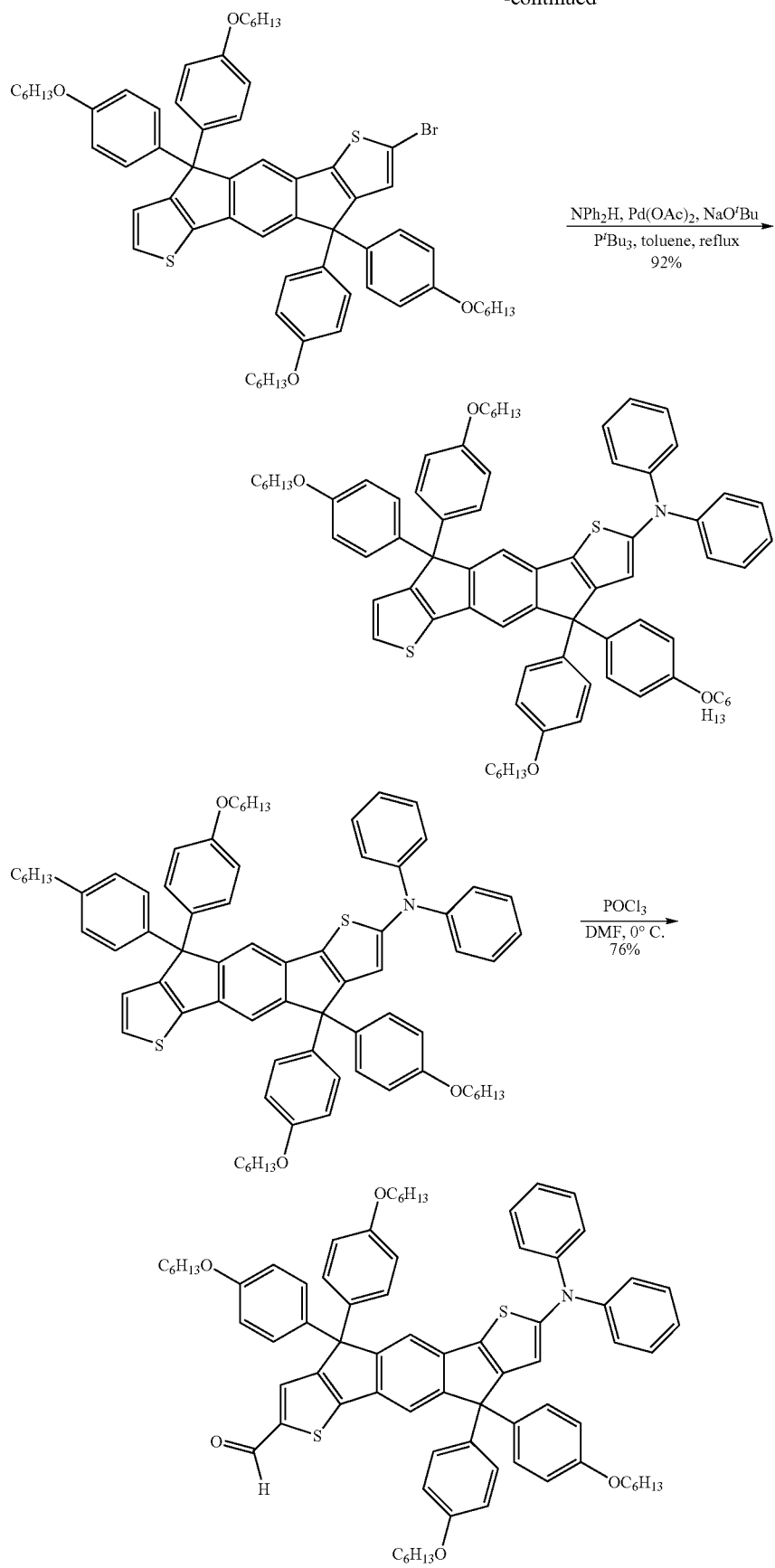

-continued
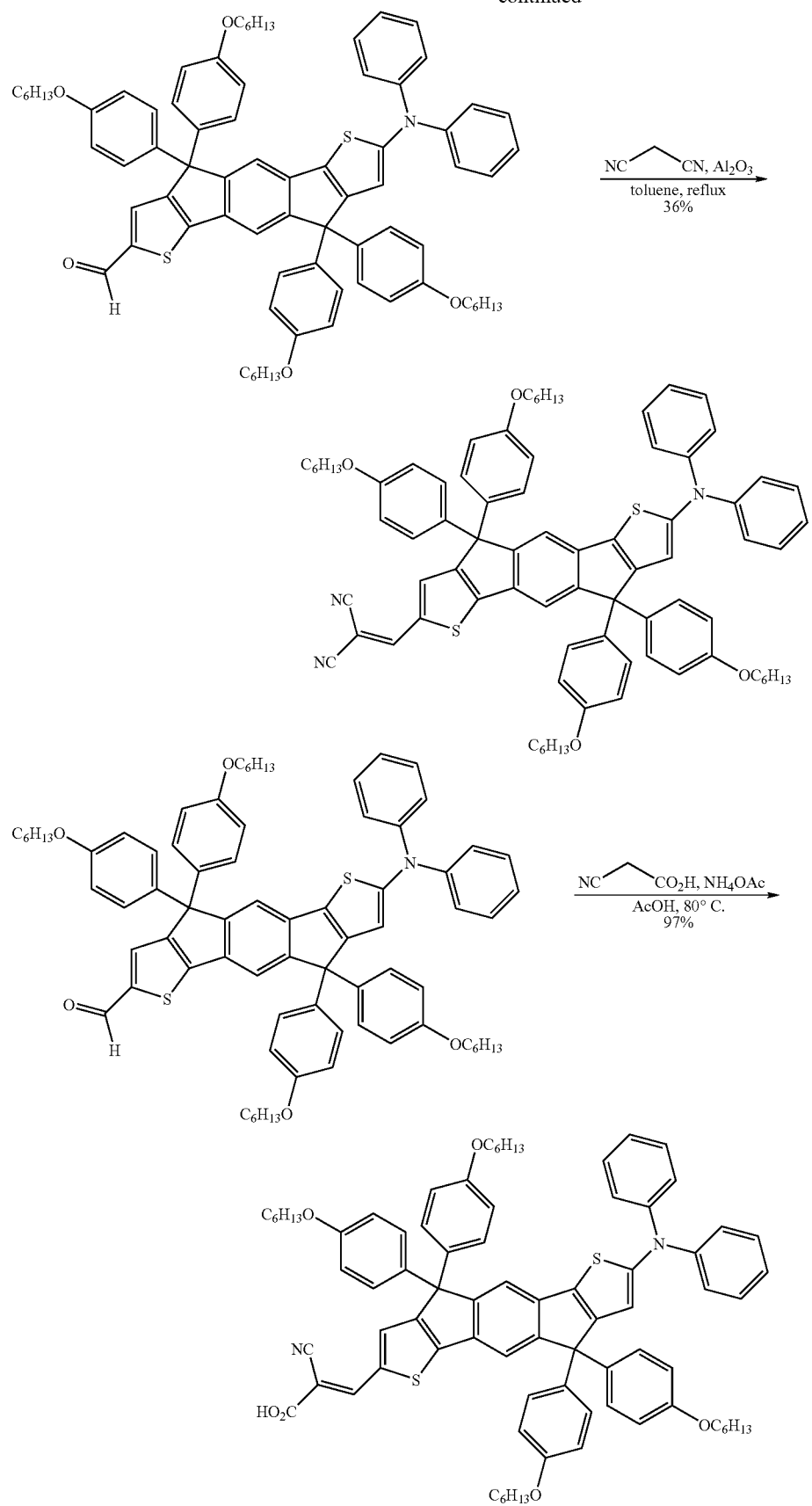

The resultant organic dye molecule of formula (2) has been characterized by the following physiochemcial data:

IR (KBr) ν 3444, 2926, 2855, 2211, 1692, 1606, 1579, 1507, 1493, 1419, 1177, 1153, 1030, 824, 696 cm$^{-1}$;

$^1$H NMR (CD$_2$Cl$_2$, 400 MHz) δ8.30 (s, 1H), 7.61 (s, 1H), 7.58 (s, 1H), 7.29-7.25 (m, 5H), 7.17-7.05 (m, 14H), 6.79-6.75 (m, 8H), 6.64 (s, 1H), 3.91 (q, J=7.06 Hz, 8H), 1.77-1.70 (m, 8H), 1.44-1.27 (m, 24H), 0.92-0.89 (m, 12H);

$^{13}$C NMR (CD$_2$Cl$_2$, 400 MHz) δ158.5, 158.3, 156.6, 156.4, 155.9, 154.6, 153.5, 153.3, 148.3, 148.3, 147.5, 139.4, 138.1, 136.0, 135.8, 135.4, 134.3, 132.8, 132.1, 129.4, 128.9, 128.8, 123.8, 123.6, 119.0, 116.5, 116.4, 115.5, 114.5, 114.4, 94.2, 68.3, 63.2, 62.4, 32.0, 30.1, 29.6, 29.5, 26.1, 23.0, 14.2; and TOF MS (m/z, ESI$^+$) 1233.

In addition, as calculated according to Beer's law, the organic dye molecule of formula (2) has a greater molar absorption coefficient (ε) of 50508 M$^{-1}$ cm$^{-1}$ (471 nm). It can been seen from FIG. 1 that the organic dye molecule of formula (2) has a broader absorption band of from about 350 nm to about 600 nm and can utilize the visible light from sunlight more efficiently.

The present invention also provides a dye-sensitized solar cell containing at least one of the diindenothiophene derivatives of formula (1). The two substrates of the solar cell of the invention can be selected from, but are not limited to, metal such as a titanium plate or stainless plate; glass; and plastic which can be, for example, but not limited to, a polyester resin, a polyacrylate resin, a polyolefin resin, a polycycloolefin resin, a polyimide resin, a polycarbonate resin, a polyurethane resin, triacetyl cellulose (TAC), or a polylactic acid or a combination thereof, and at least one of the substrates is deposited with a transparent conducting oxide (TCO) thereon to form a conducting substrate. The conducting oxide includes, but is not limited to a fluorine-doped tin oxide (FTO), an antimony-doped tin oxide (ATO), an aluminum-doped zinc oxide (AZO), or indium tin oxide (ITO). A semiconductor oxide with a nanometer-level particle size of 2-50 nm was coated onto the conducting substrate as a film with a thickness of about 5-20 μm. When the film thickness is less than 5 μm, the solar cell could not work efficiently; and on the other hand, if the film thickness is greater than 20 μm, the film is liable to crack. The semiconductor oxides that can be used in the present invention include, but are not limited to TiO$_2$, ZnO, ZrO$_2$, SrTiO$_3$, SiO$_2$ or CdS. The electrolyte that can be used in the solar cells according to the present invention can be a liquid, a gel, or a solid and a useful catalyst can be Pt or carbon black.

The dye-sensitized solar cell according to the present invention can be produced according to any method conventionally known to persons having ordinary skill in the art. For example, it can be produced by the method comprising the following steps:

(1) uniformly applying a titanium dioxide coating (produced by Solaronix company, Ti-Nanoxide HT) onto a FTO glass substrate (area: 1.7 cm×0.6 cm), to form a film with a thickness of about 11-12 μm;

(2) sintering the TiO$_2$-containing FTO glass substrate at 400° C.-600° C., to form an electrode;

(3) screen printing platinum on another glass substrate for producing a platinum electrode with a thickness of about 20 nm, as a counter electrode;

(4) immersing the electrode obtained in step (2) in, for example, a solution of the dye compound of formula (2) (solvent: 1:1 THF/Acetonitrile) for about 12-24 hours, to allow the dye compound to be absorbed to the electrode;

(5) injecting thereinto an electrolyte solution containing I$_2$, LiI, 1-propyl-3-methyl-imidazolium iodide (PMII), and methylpyrrolidinone (MPN).

The dye-sensitized solar cell containing the compound of formula (2) obtained according to the above method was tested with a simulated sunlight source (AM 1.5) at a light intensity (P) of 100 mW/cm$^2$ for measuring the current and voltage. The results are as listed in the following Table 1. The above-mentioned AM 1.5 represents an air mass 1.5 spectrum, where AM=1/cos(θ) where θ represents the tilt angle relative to the normal incidence. For testing solar cells, the average irradiance in the United States, AM 1.5 (θ=48.2°, is used to represent the average irradiance of sunlight (at 25° C.) on the earth surface with a light intensity of about 100 mW/cm$^2$.

TABLE 1

| Dye compound | Open-circuit photo-voltage$^a$ ($V_{oc}$) | Short-circuit current density Jsc$^b$ (mA/cm$^2$) | Fill factor FF$^c$ | Powder conversion efficiency η (%) |
|---|---|---|---|---|
| Formula (2) | 0.68 | −15.74 | 0.65 | 6.94 |

$^a$The voltage measured when there is no external electric current.
$^b$The output current per area of the element when there is zero load in the solar cell.
$^c$The ratio of the actual maximum obtainable power to the theoretical power of the solar cell. This is a key parameter in evaluating the performance of solar cells.

What is claimed is:

1. A diindenothiophene derivative having a structure of formula (1):

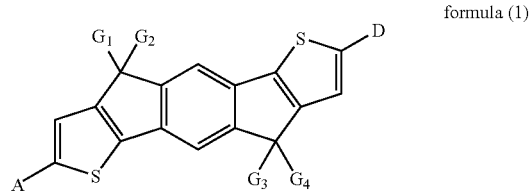

formula (1)

wherein, G$_1$, G$_2$, G$_3$ and G$_4$ are each independently an unsubstituted or substituted C$_6$-C$_{40}$-aromatic group or C$_1$-C$_{40}$-aliphatic group; A is an electron-withdrawing group; and D is an electron-donating group.

2. The diindenothiophene derivative of claim 1, wherein G$_1$, G$_2$, G$_3$ and G$_4$ are each independently an unsubstituted or substituted C$_6$-C$_{20}$-aromatic group.

3. The diindenothiophene derivative of claim 2, wherein G$_1$, G$_2$, G$_3$ and G$_4$ are each independently selected from the group consisting of formula (3), formula (4), formula (5), and formula (6):

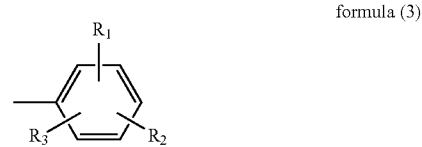

formula (3)

-continued formula (4)

[chemical structure with R1, R2, R3, R4]

formula (5)

[chemical structure with R1, R2, R3, R4, B]

formula (6)

[chemical structure with R1, R2, R3, R4, B]

wherein, $R_1$, $R_2$, $R_3$ and $R_4$ are each independently a hydrogen atom, a $C_1$-$C_8$-alkyl, or a $C_1$-$C_8$-alkoxy; and B is $CH_2$, NH, S, Si or O.

4. The diindenothiophene derivative of claim 2, wherein $G_1$, $G_2$, $G_3$ and $G_4$ are each independently

[phenyl structure] or [—C6H4—OC6H13 structure].

5. The diindenothiophene derivative of claim 2, wherein $G_1$, $G_2$, $G_3$ and $G_4$ are all

[—C6H4—OC6H13 structure].

6. The diindenothiophene derivative of claim 1, 4 or 5, wherein A is selected from the group consisting of —COOH, —CN, [CN/COOH vinyl], [CN/CN vinyl],
[(CH3)(CN)C=C(CN)(CN)], [thiophene-CH=C(CN)COOH], and
[4-methylphenyl-CH=C(CN)COOH].

7. The diindenothiophene derivative of claim 6, wherein A is

[CN/COOH vinyl] or [CN/CN vinyl].

8. The diindenothiophene derivative of claim 1, wherein D is selected from —N($S^1$)($S^2$) or —$C_6H_4$—N($S^1$)($S^2$) where $S^1$ and $S^2$ are each independently an unsubstituted or substituted $C_6$-$C_{20}$-aromatic group.

9. The diindenothiophene derivative of claim 8, wherein $S^1$ and $S^2$ are each independently selected from the group consisting of the following formula (7), formula (8), formula (9), formula (10), and formula (11):

formula (7)

[phenyl with R5, R6]

formula (8)

[naphthalene with R5, R6, R7, R8]

formula (9)

[fused bicyclic with R5, R6, R7, R8, E]

formula (10)

[fused bicyclic with R5, R6, R7, R8, B]

formula (11)

[thiophene-like with R5, R6, E]

wherein $R_5$, $R_6$, $R_7$ and $R_8$ are each independently a hydrogen atom, a $C_1$-$C_5$-alkyl or a $C_1$-$C_5$-alkoxy; and E is $CH_2$, NH, S, Si or O.

10. The diindenothiophene derivative of claim 9, wherein D is

[triphenylamine derivative structures]

-continued
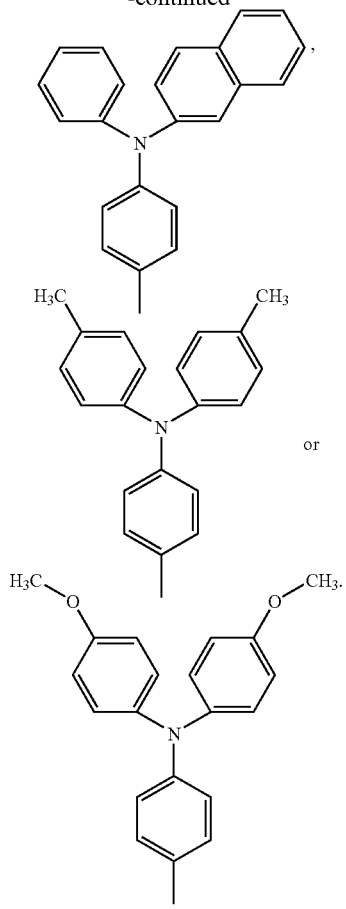
or
11. The diindenothiophene derivative of claim 10, wherein D is
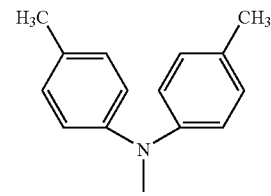
, or
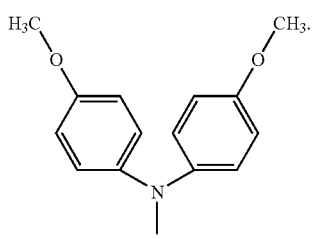
.
12. A dye-sensitized solar cell comprising a diindenothiophene derivative as claimed in claim 1.
* * * * *